United States Patent
Slautterback

(10) Patent No.: US 6,398,749 B1
(45) Date of Patent: Jun. 4, 2002

(54) ELBOW SUPPORT COMPRESSION AND METHOD

(75) Inventor: Ernest Gerald Slautterback, Coral Springs, FL (US)

(73) Assignee: FLA Orthopedics, Inc., Miramar, FL (US)

( * ) Notice: Subject to any disclaimer, the term of this patent is extended or adjusted under 35 U.S.C. 154(b) by 0 days.

(21) Appl. No.: 09/544,354

(22) Filed: Apr. 6, 2000

(51) Int. Cl.[7] ............................................... A61F 13/00
(52) U.S. Cl. ............................ 602/62; 602/60; 602/61; 2/16; 128/881
(58) Field of Search ............................ 602/20, 60, 61, 602/62; 128/877, 878, 880, 881; 2/16, 24

(56) References Cited

U.S. PATENT DOCUMENTS

| | | | | |
|---|---|---|---|---|
| 2,211,203 A | * | 8/1940 | Goldman | 128/898 |
| 3,970,081 A | | 7/1976 | Applegate | |
| 5,139,015 A | * | 8/1992 | Morneau | 602/62 |
| 5,295,951 A | * | 3/1994 | Fareed | 602/62 |
| 5,372,575 A | * | 12/1994 | Sebastian | 602/20 |
| 5,441,058 A | * | 8/1995 | Fareed | 128/898 |
| 5,624,388 A | | 4/1997 | Lehr | |
| 5,865,775 A | * | 2/1999 | Peoples et al. | 602/20 |
| 5,865,782 A | * | 2/1999 | Fareed | 602/62 |
| 6,080,124 A | * | 6/2000 | Falk et al. | 602/62 |
| 6,149,617 A | * | 11/2000 | McNally et al. | 602/62 |
| 6,216,268 B1 | * | 4/2001 | Schleicher | 2/16 |

* cited by examiner

Primary Examiner—Kim M. Lewis

(57) ABSTRACT

Disclosed is an elbow support having a C-shaped clasp body with at least one foam compression pad extending into the interior of the body for adjustable compression into the forearm of a wearer. An elongated compression strap is attached to an outer surface of the clasp body and extends around the clasp. The strap has a buckle at one end and a releasable securable device at the other end. The end with the releasable secureable device loops through the buckle and doubles back on itself for releasable attachment. This assists in securing the clasp body on the forearm and providing the adjustable compression. The elbow support is fabricated by an improved method. Pursuant to this method, a clasp body blank is cut from a sheet of thermosetting closed cell foam which is laminated with fabric. The cut clasp body blank is selectively compressed to form a compressed clasp body, from which integrally protrudes at least one compression pad in a substantially uncompressed form. The pressure strap is secured to the compressed clasp body, which is bent into an arcuate shape, and subjected to heat so that it retains an arcuate shape.

14 Claims, 4 Drawing Sheets

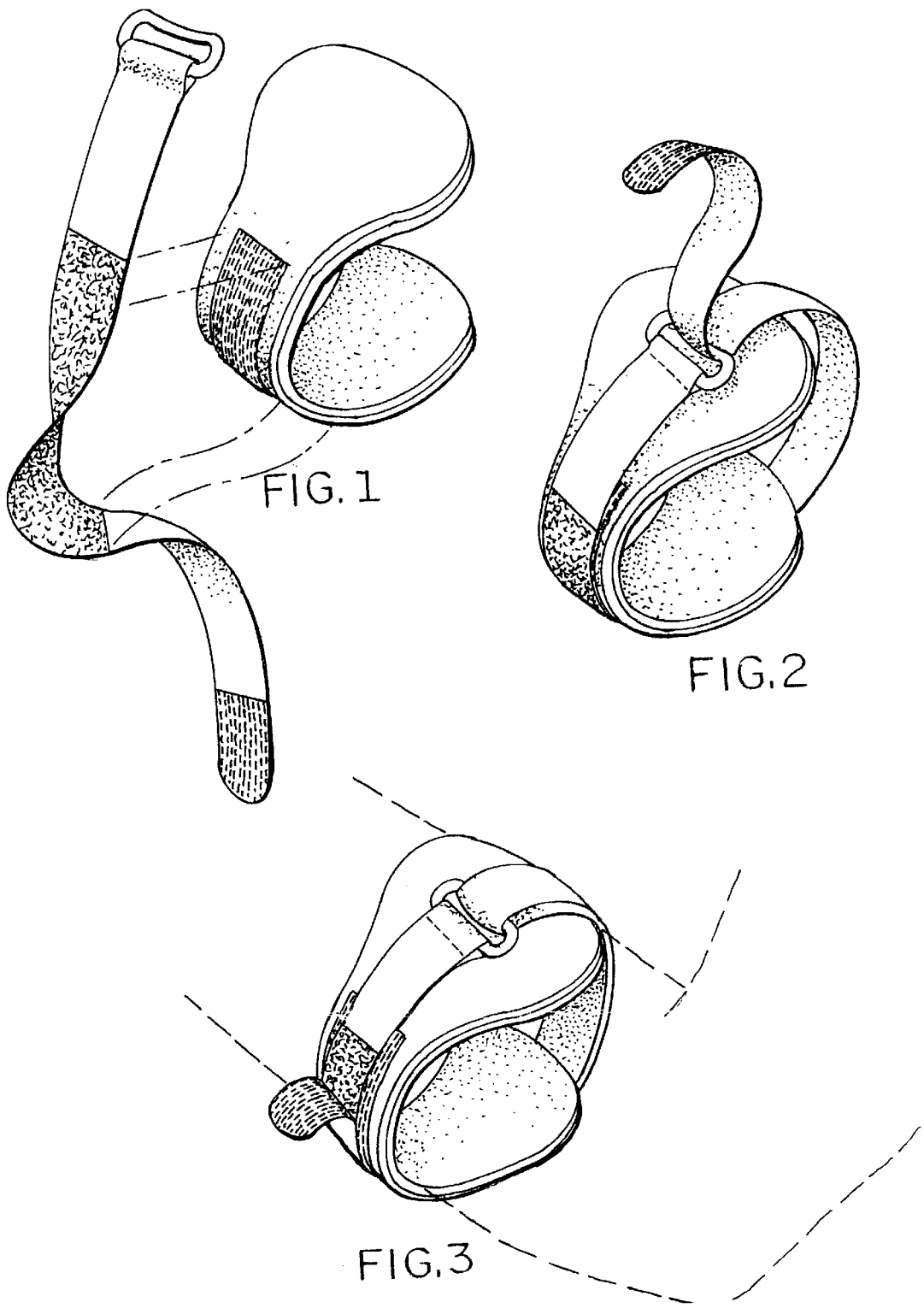

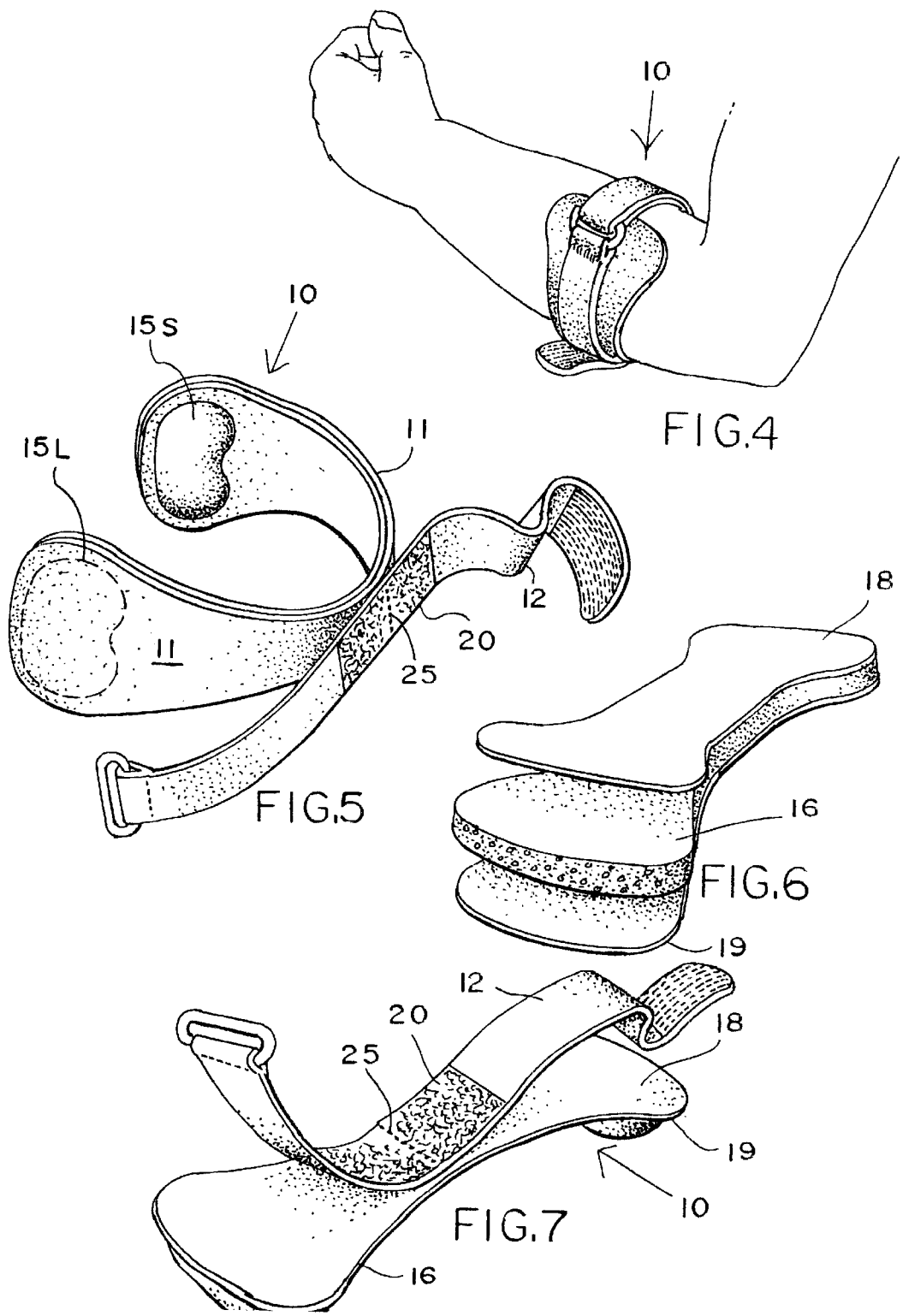

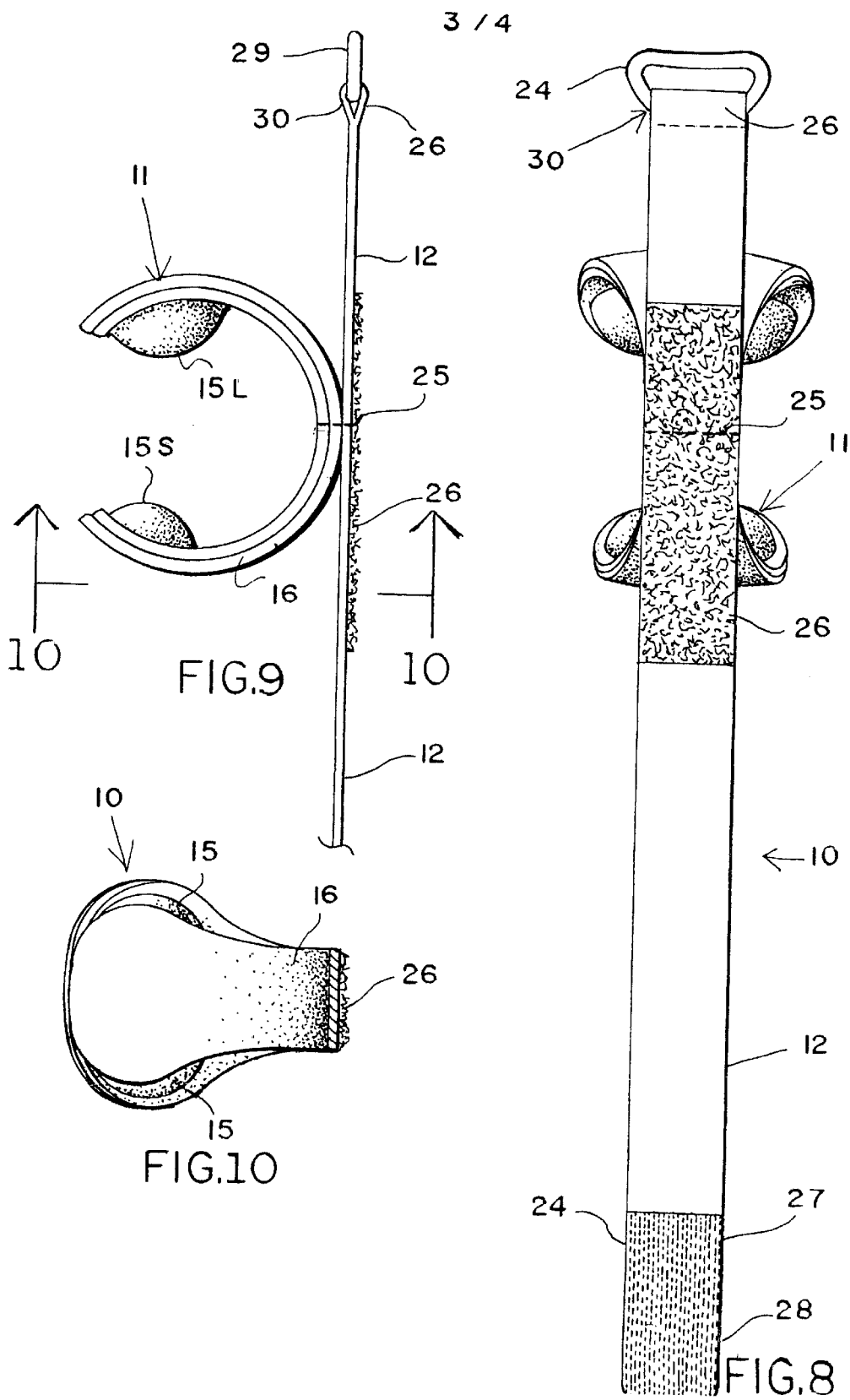

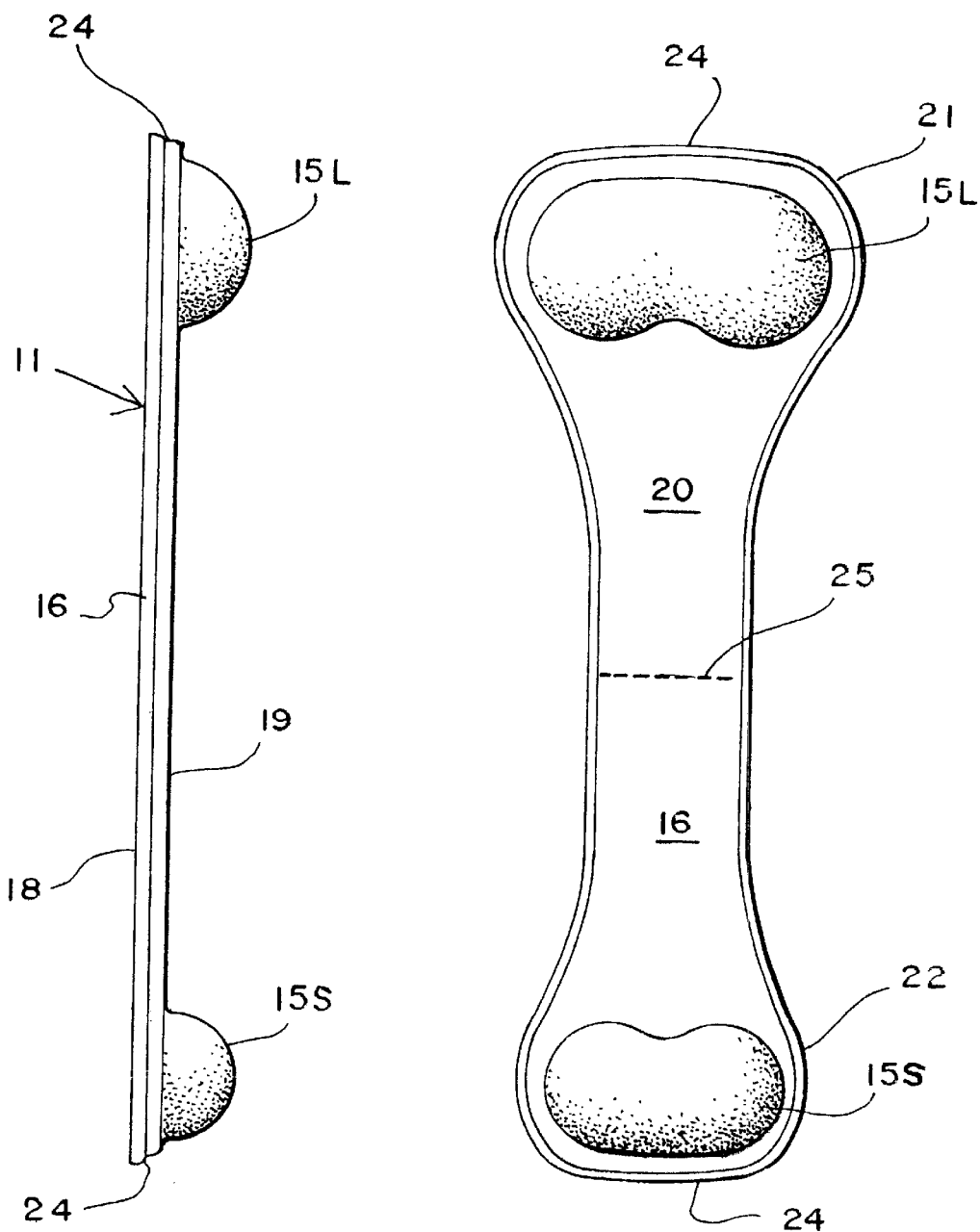

ELBOW SUPPORT COMPRESSION AND METHOD

FIELD OF THE INVENTION

The present invention relates to elbow supports and a method for fabricating the same. The purpose of the support addresses a condition known as Epicondylitis, a very common and painful injury. It comprises an inflammation of the tendons which connect the extensor and flexor muscles to the epicondyle bones of the elbow.

BACKGROUND OF THE INVENTION

Epicondylitis is an inflammation or slight tearing of tendons or muscles around the elbow joint. This can occur at the medial epicondyle, the lateral epicondyle or both. The extensor muscle group is on the lateral side (outside) of the forearm and helps turn the wrist palm up. The flexor muscle group is on the medial side (inside) of the forearm and helps turn the wrist palmdown. Tendons attach the extensor/flexor muscles to the epicondyles of the elbow. The epicondyles are the two bony knobs on either side (lateral/medial) of the elbow.

To address the epicondylitis condition, various support devices have been provided to direct lateral and medial compression and focus tendon compression. The lateral/medial compression helps the tendons and muscles remain parallel to reduce stress, pain, inflammation, and to allow healing to begin. These side by side compressions help hold the muscles and tendons in-place so that they are less bowed, stretched or unstretched. Pain from epicondylitis is greatly reduced by providing focus compression directly at the pain source, the tendons of the extensor or flexor muscles. Focused compression is achieved by the use of a separate pad in the elbow support. The pad is placed where the focus compression is needed. Products on the market have pads made of various materials such as air pillows, gel pads, and soft polyurethane foam pads.

One illustration of the prior art is found in the applicant's own product known as the Epi-Sport, manufactured and marketed by FLA Orthopedics, Inc. subsidiary Clinitex Medical Corp. The Epi-Sport product utilizes a curvilinear body or clasp of synthetic material to encircle more than 180 degrees of the forearm closely adjacent to the elbow. Optionally, one end portion is wider than the other end portion, with the two end portions and the intervening medial portion defining a clasp having a C shaped cross-section. The clasp relies on its shape to apply pressure on the tendons of the forearm. An elongated compression strap is secured to the outside of the medial portion of the C shaped body on the outside, and extends in both directions. One end of the strap terminates in a buckle, and the other terminates in a reversely foldable member. The reversely foldable member carries a releasable securable material on one surface. The back or outside of the medial portion of the strap also carries a section of a releasable securable member. When the strap is pulled snug, it can easily be secured in-place with one hand by mating the two releasable securable members.

SUMMARY OF THE INVENTION

The present invention is directed to improved elbow supports which are generally similar to the described prior art supports. More particularly, the invention is directed to a unique method for fabricating such devices. The elbow support comprises a curvate clasp having a generally C shaped cross section, with the clasp encircling the forearm of the wearer in excess of 180 but less than 360 degrees. In one preferred embodiment the clasp carries an inner compression pad at each of its ends. These oppositely disposed pads are designed to focus compression to hold the muscles and tendons in place. The clasp is itself encircled by an attached strap, which may be tightened to secure the desired amount of compression from the pads.

In fabricating the elbow support, the material for forming the clasp is first prepared by forming a laminated composite material. The laminated composite material preferably comprises a flat sheet of a compressible heat formable closed cell foam, which is sandwiched between surface sheets of fabric. The fabrics are adhesively or otherwise attached to the sheet foam. The foam may be formed of any of a number of suitable synthetic materials, such as polypropylene, urethane, polyurethane, olefin, polyolefin, and similar materials. One example of such a material is a polyolefin film marketed under the trademark Volara.

The inner liner, or fabric covering the inner surface of the foam sheet, is preferably of a soft material. The inner fabric ideally is capable of moving moisture, but this is not essential. One example of a satisfactory inner fabric is a material sold under the trademark Orthowick, which wicks moisture. On the other hand, polypropylenes, polyesters, cottons, acrylics, cellulose acetates, spandex, and other such fabrics are also suitable. The fabric covering the outer surface of the support clasp is chosen for its durability and appearance. This outer fabric may be formed of a nylon mesh, or similar primarily knitted type long wearing material. Neither the inner nor the outer fabric material is critical, and numerous similar fabrics may be used.

The composite fabric-foam-fabric laminate is next die cut or otherwise cut to the desired clasp body shape to create an uncompressed clasp body blank. The edges of this laminated clasp blank may then be sewn to provide a neat and attractive binding. The strap also may optionally be attached at this time, such as by sewing or other suitable means such as adhesive.

The thus assembled clasp body blank is then subjected to selective compression and forming into the desired C shaped form. The compression is selectively applied, so as provide in the C shaped clasp a sufficiently high density to furnish the desired rigidity. At the same time the compression step also provides one or more substantially uncompressed integral pressure pads. The clasp body is generally of a substantially uniform density over the major portion of its body, with the exception of the pressure pads. The pressure pads have a lesser density than the remainder of the compressed body, and may not have been subjected to significant compression. In any event, they form integral, generally bulbous protrusions from the inner end surfaces of the clasp body. These protrusions are disposed in a manner to provide compression against the tendons in the forearm at the desired point or points. The pressure pads may be pre-lined with fabric through the use of the preformed laminated closed cell foam material. On the other hand cut outs may be formed for the pressure pads, so that they are unlined.

The clasp is compressed and formed into its C shaped configuration under heat and pressure. It is in the nature of the closed cell foam of which the clasp is formed that it will retain its formed shape and density after the heat and pressure are removed.

Accordingly, it is a principal object of the present invention to provide an improved elbow support having integral compression pads fabricated pursuant to an efficient and economical new method.

It is another object of the invention to provide a new, effective and economical method for fabricating improved elbow supports having integral pressure pads which are accurately disposed using minimal method steps.

It is another object of the invention to provide a method for fabricating a wrist support by procuring for the clasp body a composite sheet material comprising a synthetic resin foam sandwiched between fabric liners, cutting the sheet to define a clasp body blank, selectively compressing the composite sheet material forming the blank to form at least one substantially uncompressed compression pad of foam, attaching a strap to the clasp body, and forming the clasp body into a curvate shape.

It is another object of the invention to provide an elbow support comprising a generally C-shaped clasp body having at least one foam compression pad extending into the interior of the body for adjustable compression into the forearm of a wearer, an elongated compression strap attached to an outer surface of the clasp body and extending therearound, the strap having a buckle at one end and a releasable securable device at the other end which loops through the buckle and doubles back on itself for releasable attachment to assist in securing the clasp body on the forearm and providing the adjustable compression, wherein the elbow support is fabricated by an improved method comprising the steps of cutting clasp body blanks from a sheet of thermosetting foam which is laminated with fabric, selectively compressing at least one of the cut clasp body blanks to form a compressed clasp body from which the compression pad integrally protrudes in a substantially uncompressed form from one end portion of the compressed clasp body, securing the pressure strap to the compressed clasp body, bending the compressed clasp body into an arcuate shape, and subjecting the bent clasp body to heat so that it retains an arcuate shape.

DESCRIPTION OF THE DRAWINGS

Further objects and advantages of the present invention will become apparent from the following description of an illustrative embodiment as illustrated in the appended drawings wherein:

FIG. 1 is a perspective view of a prior art elbow support showing in exploded relationship the strap and the clasp portion.

FIG. 2 is a perspective view of the elbow support of FIG. 1 showing the elbow support in an assembled condition prior to mounting on the forearm of a user.

FIG. 3 is a further perspective view showing the prior art elbow support of FIGS. 1 and 2 secured to the forearm of the user, the forearm being shown in phantom lines.

FIG. 4 is a view comparable to that of FIG. 3, illustrating the position of the clasp and strap of the elbow support of the invention on the arm of the user.

FIG. 5 is a perspective view of the elbow support of the invention.

FIG. 6 is an exploded view of the clasp of the elbow support of the invention at an early stage of fabrication.

FIG. 7 is a sequential view of the elbow support of the invention with the strap attached.

FIG. 8 is an elongated plan view of the elbow support of the invention showing the strap and its releasable securable elements in plan view.

FIG. 9 is a side elevation view illustrating the curved clasp body along with its associated strap.

FIG. 10 is an enlarged end view of the clasp taken from section 10—10 of FIG. 9.

FIG. 11 is a plan view of the clasp prior to curving.

FIG. 12 is a side elevation of the elbow support shown in FIG. 11. Both FIGS. 11 and 12 are illustrative of the product prior to the attachment of the strap and curving of the clasp to the configuration shown essentially in FIG. 9.

DESCRIPTION OF THE PREFERRED EMBODIMENT

As an aid to understanding of the features of the invention, a typical prior art device is illustrated in FIGS. 1, 2, and 3. As may be seen in FIG. 1, this device includes a clasp portion and associated strap, which may be attached to the clasp portion. The strap is secured around the clasp and wearer's arm by threading through the buckle to form a lock loop closure. This is shown in FIG. 2. In its mounted position on the forearm of a wearer, as shown in FIG. 3, the clasp and strap surround the forearm of the user close to the elbow. It will be noted that this prior art device lacks interior focus pressure pads, which sometimes are provided in the prior art. In this device, the laterally enlarged ends of the clasp are relied upon to supply the desired compression to the tendons of the forearm extensor and flexor muscles.

Referring to FIG. 4, there is shown in a partially broken perspective view, an elbow support of the invention, indicated at 10, encircling the forearm of a wearer. FIG. 5 shows the elbow support 10 in a dismounted perspective view. The compression strap is indicated at 12 attached to the C shaped clasp body 11. The attachment of the strap to the clasp may be by any suitable means, and is preferably sewn along a lateral line of stitching, as is shown at 25. The C shaped clasp 11 carries bulbous pressure pads at its inner ends, as shown at 15S and 15L. Depending upon the elasticity of the inner liner fabric, these pads may be covered by the liner or may pass through cut-outs therein.

According to the preferred embodiment of the invention the C shaped clasp body 11 is formed of a laminate, as best shown in the partly exploded view of FIG. 6. The laminate comprises an essentially flat sheet of a heat compressible and formable closed cell foam 16, which is sandwiched between fabric surface sheets 18 and 19. The foam 16 may be formed of any of a number of suitable materials, such as polypropylene, urethane, polyurethane, olefin, polyolefin, and similar closed cell foams. One such material is commercially available under the trademark Volara. The initial thickness of the foam sheet is greater than its terminal thickness at the conclusion of compression. Likewise, the initial density of the foam sheet is lower than its terminal density at the conclusion of compression.

The outer laminate fabric 18 is chosen for its durability and appearance. This outer fabric may be formed of a nylon mesh, or similar primarily knitted type long wearing material. The inner laminate fabric 19 covers the inner surface of the clasp, next to the skin of the wearer. This fabric is preferably formed of a soft material. The inner fabric ideally is capable of moving moisture, but this is not essential. One such fabric which is commercially available is sold under the trademark Orthowick, as previously mentioned. This material has the property of wicking moisture. On the other hand, polypropylenes, polyesters, cottons, acrylics, cellulose acetates, spandex, and other such fabrics are also suitable.

The composite laminate from which the clasp is formed is provided in sheet form with the outer fabrics adhesively or otherwise attached to the foam. The "dog bone" shaped clasp body, as generally seen in FIG. 6, is then cut from the composite sheet material by a suitably shaped die or equivalent cutting operation to form the clasp body blank. It will be appreciated that the thickness of the foam in the composite material shown in FIG. 6 is the pre-compression thickness. This thickness is basically the same as the thickness of the post compression pressure pads. Neither FIG. 6 nor any of the other figures showing relative dimensions are intended to be to scale.

It will be appreciated that the compression step may subject the pressure pads to a degree of forming into their bulbous shapes. However, the pads remain essentially uncompressed so as to be capable of providing the desired focused compression against the tendons and muscles. The post compression appearance of the clasp body 16 is best seen in FIGS. 11 and 12. FIG. 11 shows the clasp body to comprise a central portion 20, from which the clasp body extends in opposite directions to the clasp ends 24. One of the clasp ends 21 is preferably larger than the opposite clasp end 22. The larger end 21 contains the larger compression pad 15L, while the smaller end contains the smaller compression pad 15S. The broken line 25 in FIG. 11 shows the position wherein the strap may be laterally sewn to the clasp.

FIG. 12 shows a side view of the post compression clasp body. The substantially uncompressed pressure pads 15L and 15S protrude integrally from the compressed clasp body. The pressure pads may protrude through cut-outs in the inner liner 19, or may be covered by the inner liner. The repetitive assembly process of die cutting and selective compression in molds assures precise correct placement of the pressure pads. Following formation of the clasp bodies 11 into the shapes seen in FIGS. 11 and 12, they are curved and subjected to the appropriate degree of heat to cause the particular synthetic material to set into the desired curvate shape. This curvate shape in the clasp is seen in FIGS. 4, 5, and 9.

Either before or after curving the clasp body 16, the compression strap 12 is attached. This strap is best seen in FIGS. 8 and 9. The compression strap 12 is an elongated element of fabric material terminating at a strap hook end 28. The strap hook end is covered with an elongated strip of hook fastener 27. The other end of the strap terminates in a strap loop 30 in which is sewn a buckle 29.

The compression strap 12 also has applied to a medial section of its outer side, a loop portion 26 of a material for forming a releasable hook and loop fastening. This loop material is fastened to be outside of the strap at the point where the strap is sewn to the clasp, as shown by the stitch line 25 in FIGS. 8 and 9. While the strap has been shown and described as attached to the clasp by stitching, it is equally acceptable to utilize other means of fastening, such as adhesives, heat sealing, or other techniques.

The strap hook material 27, which is intended to fasten to the loop material 26, is found at the lower end of the strap 12 as seen in FIG. 8. When the elbow support clasp is secured onto a wearer, the lower end of the strap 12 with its hook material 27 passes through the buckle 29 to pull the strap tight. When the tensioned strap reaches this position, it is looped back onto itself so that the hook material 27 releasably secures to the loop material 26. This tightening operation is easily performed with the free hand of the wearer. The strap provides adjustable securement for applying the desired amount of pressure from the pressure pads 15L and 15S.

It will be apparent from the foregoing that the uniquely fabricated elbow support of the invention satisfies its objective of providing an improved elbow support which is fabricated by a unique and improved method. The method of fabrication is simple and economical and provides a high degree of uniformity in the elbow support product which is produced.

It will be readily seen by one of ordinary skill in the art that the present invention fulfills the objects and objectives set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

What is claimed is:

1. A method of fabricating an elbow support comprising:
   cutting from a sheet of thermosetting foam laminated with fabric, elbow support clasp blanks;
   selectively compressing at least one of said cut clasp blanks to form a compressed clasp having at least one substantially uncompressed pressure pad integrally protruding from one end portion of said compressed clasp;
   securing an elongated pressure strap to the clasp;
   bending said clasp into an arcuate shape; and
   subjecting the bent clasp to heat so that it retains an arcuate shape.

2. The method according to claim 1 wherein said foam is a closed cell foam.

3. The method according to claim 2 wherein said closed cell foam is laminated between a durable fabric on one surface and a soft fabric on the opposite surface.

4. The method according to claim 3 wherein said durable fabric is selected from synthetic fabrics having substantially the durability characteristics of a nylon fabric.

5. The method according to claim 4 wherein said soft fabric is selected from fabrics having substantially the softness characteristics of a cotton fabric.

6. A method of fabricating an elbow support comprising:
   cutting from a sheet of thermosetting foam, elbow support clasp blanks;
   selectively compressing at least one of said cut clasp blanks to form a compressed clasp having at least one substantially uncompressed pressure pad integrally protruding from one end portion of said compressed clasp;
   securing an elongated pressure strap to the compressed clasp;
   bending said compressed clasp into an arcuate shape; and
   subjecting the bent clasp to heat so that it retains an arcuate shape.

7. The method according to claim 6 wherein said foam is a closed cell foam.

8. The method according to claim 6 wherein the foam sheet is of a material selected from the group consisting of polypropylene, urethane, polyurethane, olefin, and polyolefin.

9. The method according to claim 6 wherein the foam sheet is laminated between fabric sheets.

10. The method according to claim 9 wherein said fabric sheets comprise different fabrics.

11. The method according to claim 6 wherein said thermosetting foam is laminated between a durable fabric on one surface and a soft fabric on the opposite surface.

12. The method according to claim 11 wherein said durable fabric is selected from synthetic fabrics having substantially the durability characteristics of a nylon fabric.

13. The method according to claim 12 wherein said soft fabric is selected from fabrics having substantially the softness characteristics of a cotton fabric.

14. A method of fabricating an elbow support comprising:

forming a composite laminate sheet having a compressible closed cell foam core sandwiched between different fabric surface materials;

cutting from the laminated composite sheet, elbow support clasp blanks;

subjecting at least one of said elbow support clasp blanks to selective compression to form compressed clasps having at least one substantially uncompressed pressure pad integrally protruding from one end portion thereof;

securing an elongated pressure strap to the compressed clasp;

bending said elbow support clasp into an arcuate shape and subjecting the arcuate clasp to heat whereby the clasp retains an arcuate shape following the completion of the heat treatment.

* * * * *